(12) United States Patent
Safai et al.

(10) Patent No.: US 7,535,990 B2
(45) Date of Patent: May 19, 2009

(54) LOW PROFILE VISION SYSTEM FOR REMOTE X-RAY INSPECTION

(75) Inventors: Mortenza Safai, Seattle, WA (US); Gary Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 165 days.

(21) Appl. No.: 11/615,639

(22) Filed: Dec. 22, 2006

(65) Prior Publication Data

US 2008/0152084 A1    Jun. 26, 2008

(51) Int. Cl.
*G01N 23/083* (2006.01)
*G01T 1/20* (2006.01)
*H01L 27/142* (2006.01)

(52) U.S. Cl. .............................. 378/63; 378/57; 378/62; 250/368; 250/370.09

(58) Field of Classification Search .................... 378/57, 378/58, 62, 63, 98, 98.2, 98.3, 98.5, 98.8, 378/98.12, 210; 382/141, 149–152; 250/362, 250/363.01, 368, 370.01, 370.08, 370.09, 250/371
See application file for complete search history.

(56) References Cited

U.S. PATENT DOCUMENTS

| | | | | | |
|---|---|---|---|---|---|
| 4,052,621 | A | * | 10/1977 | Haas | 250/458.1 |
| 5,127,032 | A | * | 6/1992 | Lam et al. | 378/189 |
| 5,590,170 | A | * | 12/1996 | Zweig | 378/63 |
| 6,272,204 | B1 | * | 8/2001 | Amtower et al. | 378/63 |
| 7,198,404 | B2 | * | 4/2007 | Navab et al. | 378/206 |
| 7,330,583 | B2 | * | 2/2008 | Clark et al. | 382/149 |
| 2004/0174950 | A1 | * | 9/2004 | Polichar et al. | 378/98.2 |
| 2005/0089142 | A1 | * | 4/2005 | Marek | 378/98.8 |
| 2005/0148876 | A1 | * | 7/2005 | Endoh et al. | 600/454 |
| 2005/0156113 | A1 | * | 7/2005 | Suzuki et al. | 250/368 |
| 2005/0276379 | A1 | * | 12/2005 | Polichar et al. | 378/98.2 |
| 2007/0019787 | A1 | * | 1/2007 | Zuckier | 378/63 |
| 2007/0104315 | A1 | * | 5/2007 | Kim et al. | 378/58 |

* cited by examiner

*Primary Examiner*—Edward J Glick
*Assistant Examiner*—Anastasia Midkiff
(74) *Attorney, Agent, or Firm*—Brosemer, Kolefas & Associates LLC

(57) ABSTRACT

A low-profile real-time x-ray detector has a visual sensor that provides a wide angle visual image of a location on an inspected part that is being imaged by x-rays. Fish eye lenses in the visual sensor view a reflection of a part being inspected from a highly reflective surface mirror on an x-ray sensitive surface. The visual sensor may provide an exact visual replica of the area on the inspected part that is being imaged by x-rays.

11 Claims, 5 Drawing Sheets

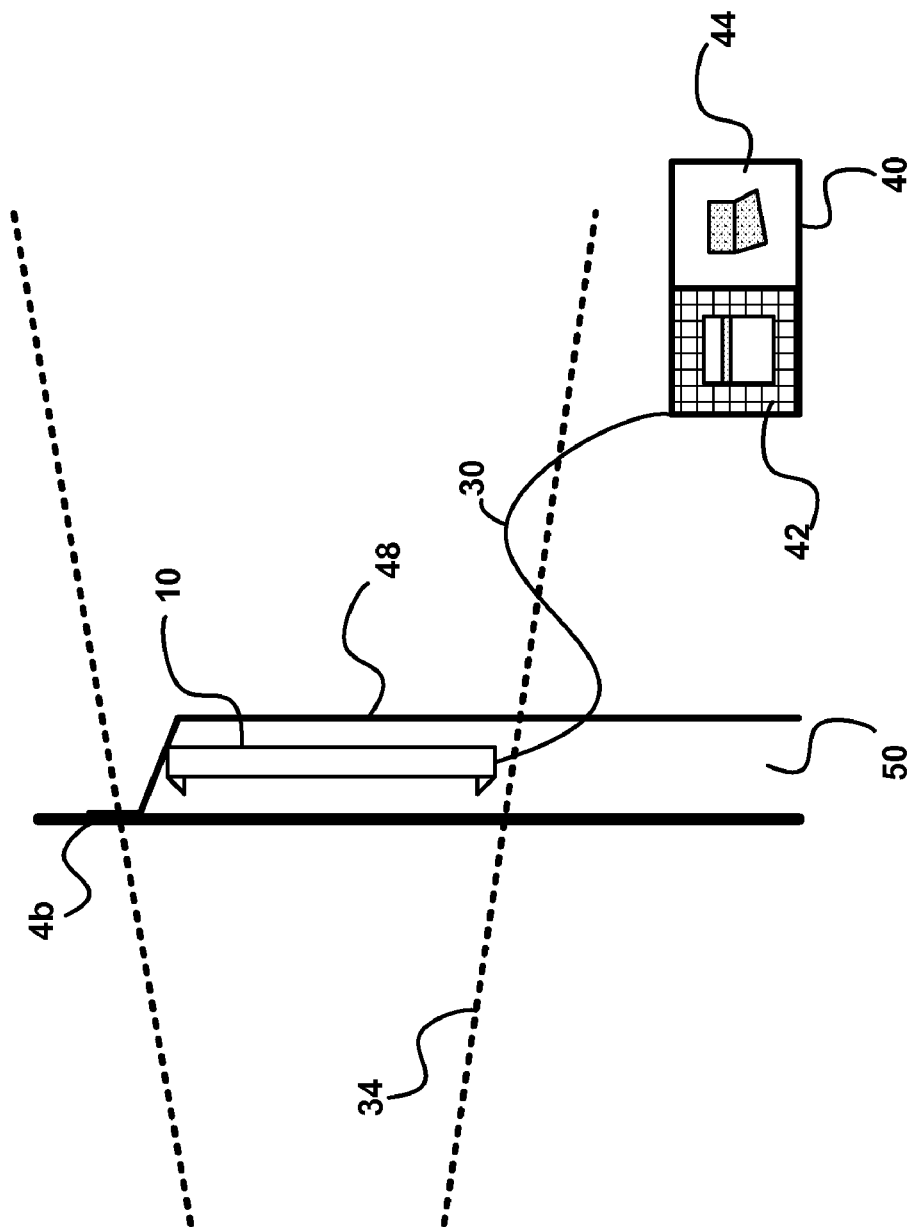

LOW PROFILE VISION SYSTEM FOR REMOTE X-RAY INSPECTION

TECHNICAL FIELD

This disclosure relates to imaging. More particularly, this disclosure relates to the provision of visual information correlated to x-ray data to improve inspection of certain structures such as aerospace structures.

BACKGROUND

With the increasing use of unitized and complex aerospace structures, there is a critical need for technologies that allow for Non-Destructive Inspection (NDI) in locations of the structure that are not easily accessible. Limited Access NDI (LANDI) is an emerging field of interest being pioneered to support programs such as Sea Launch, and the Boeing 787 aircraft. Utilizing innovative LANDI approaches, ultrasonic, visual, and x-ray techniques, among others, can be applied to composite and metal aircraft sub-structure.

X-ray inspection methods are often the most suitable for certain structures, due to the type or size of defects or damage that must be found, or the nature of the structure or material under inspection. The problem is that interpretation of the x-ray data taken in a limited access area (such as a hat stiffener on the 787 fuselage) is very difficult because the area cannot be seen with the naked eye or traditional cameras.

A capability of providing visual information that directly correlates to the x-ray data would provide several key advantages. Precise visual information is extremely advantageous when determining the location, size, and shape of defects or damage. Many features on an x-ray image may be mis-identified as defects or damage, but may simply be surface features due to manufacturing processes or foreign objects. The depth of the feature on an x-ray image may require multiple shots, using parallax principles. However, visual inspection of the area would often eliminate the need for multiple shots (also reducing x-ray exposure), if the feature is actually on the surface.

There are no techniques currently in existence that correlate x-ray data with visual information to achieve the advantages listed above. Optical borescopes exist that can provide remote visual inspection within structures. However, even if they were to be attached to an x-ray detector to provide visual information, there would be no adequate way to directly correlate the visual and x-ray images. Positioning of cameras that might provide better correlation is not possible for limited access areas, due to limited head space.

SUMMARY

This invention provides real time optical (visual) inspection during limited or remote access x-ray inspection. It allows superimposition of the x-ray and visual images, offering significant improvement in data interpretation.

BRIEF DESCRIPTION OF THE DRAWINGS

FIG. 5 shows an application of the inspection system of FIGS. 1, 2, and 3 to the inspection of a structure providing limited access for inspection.

DETAILED DESCRIPTION

Figure 1:
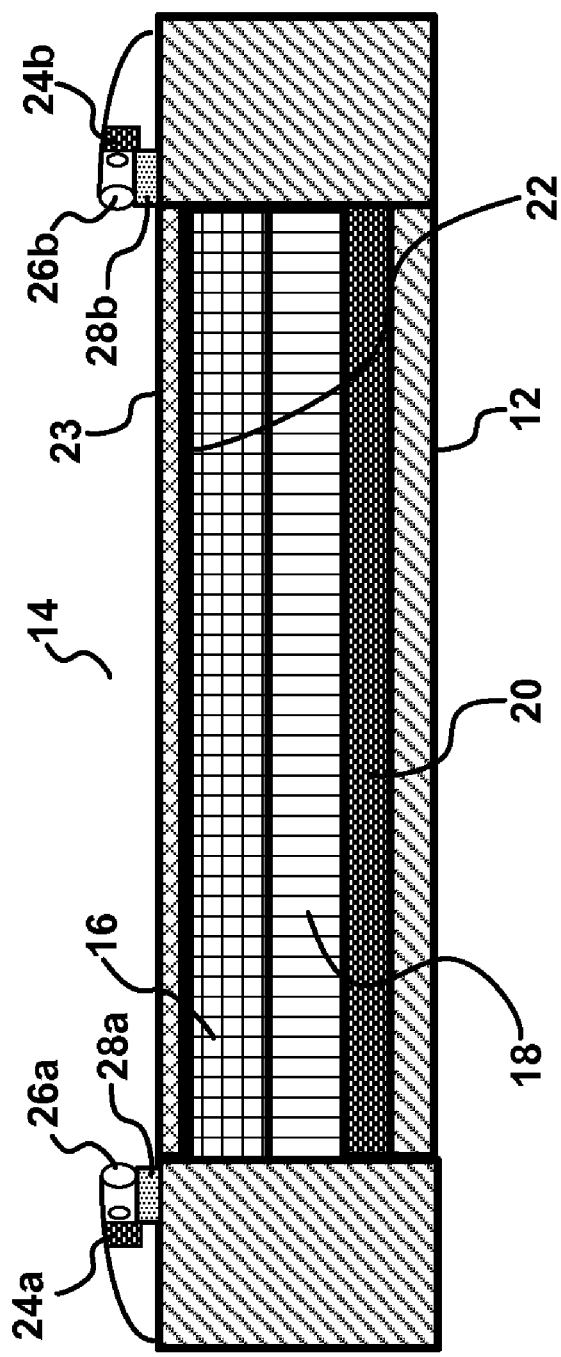
FIG. 1 is a side sectional view of a low profile inspection system in accordance with one example of the invention.
Figure 2:
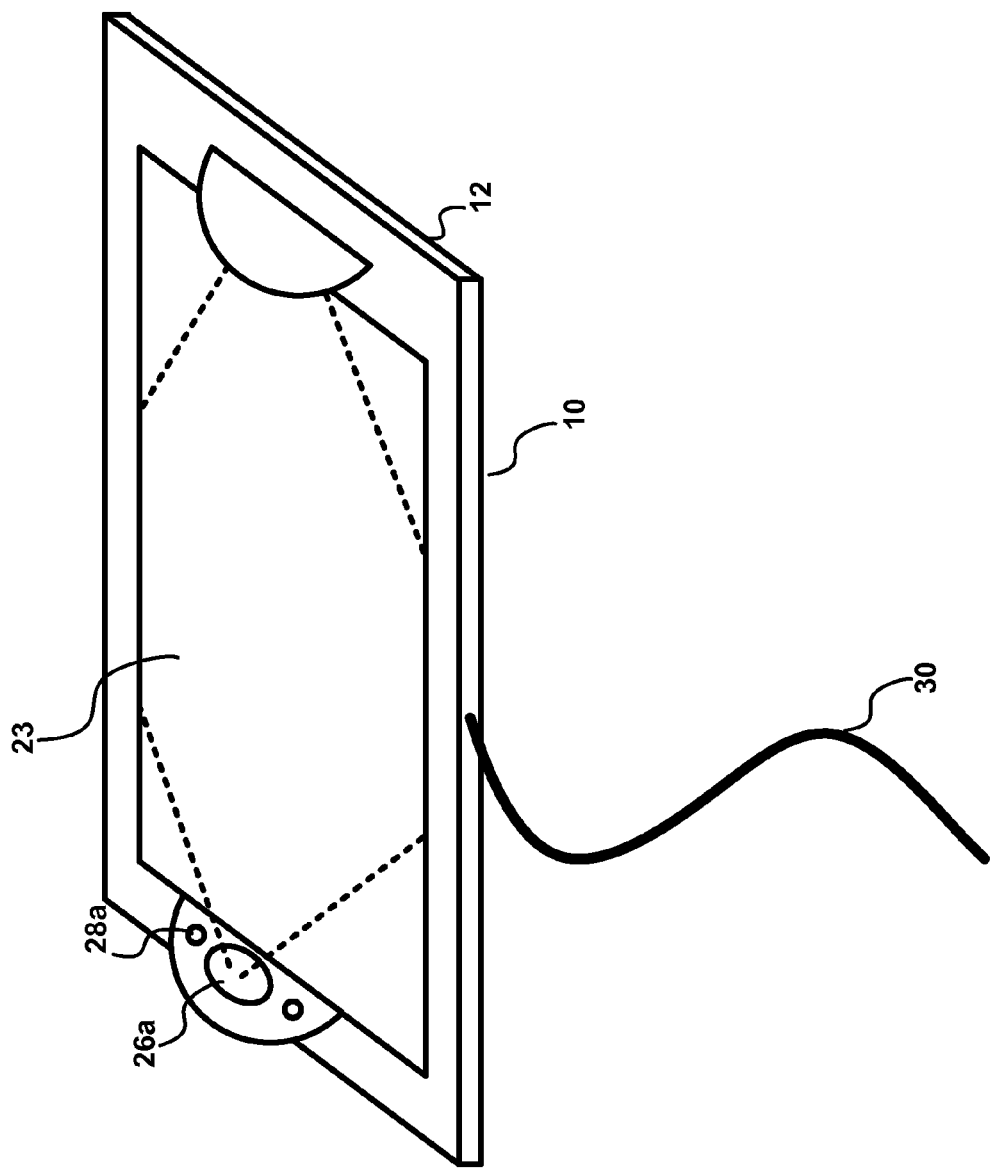
FIG. 2 is a perspective view of the inspection system of FIG. 1.
Figure 3:
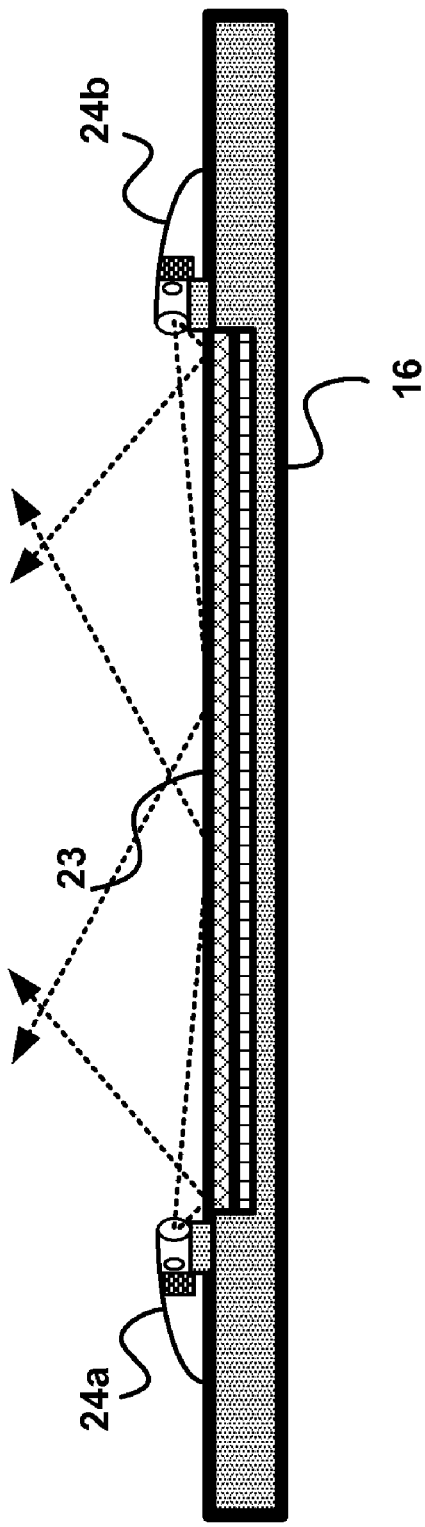
FIG. 3 is a drawing illustrating a typical field of view of the cameras used with the inspection system of FIGS. 1 and 2.

FIGS. 1, 2, and 3 illustrate an example of an inspection system in accordance with the invention. The inspection system of FIGS. 1, 2, and 3 has one or more miniature cameras with wide angle lenses mounted on an x-ray detector to provide a visual image corresponding to an x-ray image produced by the detector. The x-ray detector produces an electrical output signal in accordance with the intensity of x-rays falling on the detector. Those x-rays may be produced by an x-ray source not shown in FIG. 1 that directs x-rays through a part being inspected.

The invention is not limited to any particular form of x-ray detector. In the example of the invention shown in FIGS. 1, 2, and 3 the x-ray detector 10 comprises a flat rectangular casing 12, which has a generally planar front side 14 which receives x-rays from an x-ray source. The detector 10 comprises a generally rectangular array of x-ray scintillators 16 that overlay a silicon based detector array 18. The array 18 is supported by an electronics substrate 20. A thin film plastic isolator film 22 protects the x-ray sensitive surface of the scintillator array 16.

The scintillator array 16 receives x-rays and converts the x-rays into light. The detector array 18 converts the light output of the scintillator array 16 into electrical energy corresponding to the magnitude of the x-rays falling on the detector 10. The electrical output of the array 18 is transmitted on a cable 30 to an image storage and display device. The image storage and display device may be a programmed digital computer having a display that can show an image of the part being inspected.

In this example of the invention, a thin coating 23 is applied to the front side 14 of the x-ray detector 10. This coating 23 is highly optically reflective, and acts as an optical mirror. The specific chemical composition of the coating is not critical as long as it is transparent to x-rays and optically reflective. Examples of materials that may be used as the coating 23 include silicon oxide and alumina.

Small miniature CCD or CMOS cameras 24a and 24b each with respective wide angle lenses 26a and 26b, are mounted just above the surface 14 of the detector 10 on the sides of the casing 12 near the edges of the coating 23. The two cameras 24a and 24b produce wide angle optical images reflected from the coating 23. Examples of wide angle optics that may be employed in the cameras 24a and 24b to produce wide angle images include one or more fisheye lenses. The cameras 24a and 24b are oriented so that the area of the coating 23 to be imaged is within the field of view of the cameras 24a and 24b. The dotted lines in FIGS. 2 and 3 illustrate representative fields of view of the cameras 24a and 24b. In the example of the invention shown in FIG. 1, the optical axes of the cameras are substantially parallel to the surface 14 of the x-ray detector 10 and located a short distance above that surface 14.

FIGS. 1, 2, and 3 show two cameras being used to create visual images corresponding to the x-ray image produced by the detector 10. The invention, however, is not limited to any particular number of cameras. The number of cameras to be used and their locations on the detector 10 is determined by the extent of the reflective coating surface 23 to be imaged and the fields of view of the cameras.

The cameras are low profile, and provide higher resolution images than fiber-optic borescopes. The reflected real-time images from the cameras are conveyed to the previously mentioned image storage and display device along with the x-ray image from the detector 10, where image processing software may be used to stretch or otherwise manipulate the x-ray and visual images to provide a required display of the two images. Light emitting diodes (LED's) 28a and 28b at the edge of the detector 10 can be used to illuminate the area being imaged. All this is accomplished with a very low profile, so very narrow substructures can be inspected.

This system is capable of providing a real time visual image correlated to an x-ray image is being taken, allowing superposition of the images or side by side comparison of the images for improved analysis and interpretation. This technique can be applied to any size or shape x-ray recording medium (digital or film), as long as it can lie relatively flat and provide an optical reflection that can be recorded and digitally manipulated.

Figure 4:
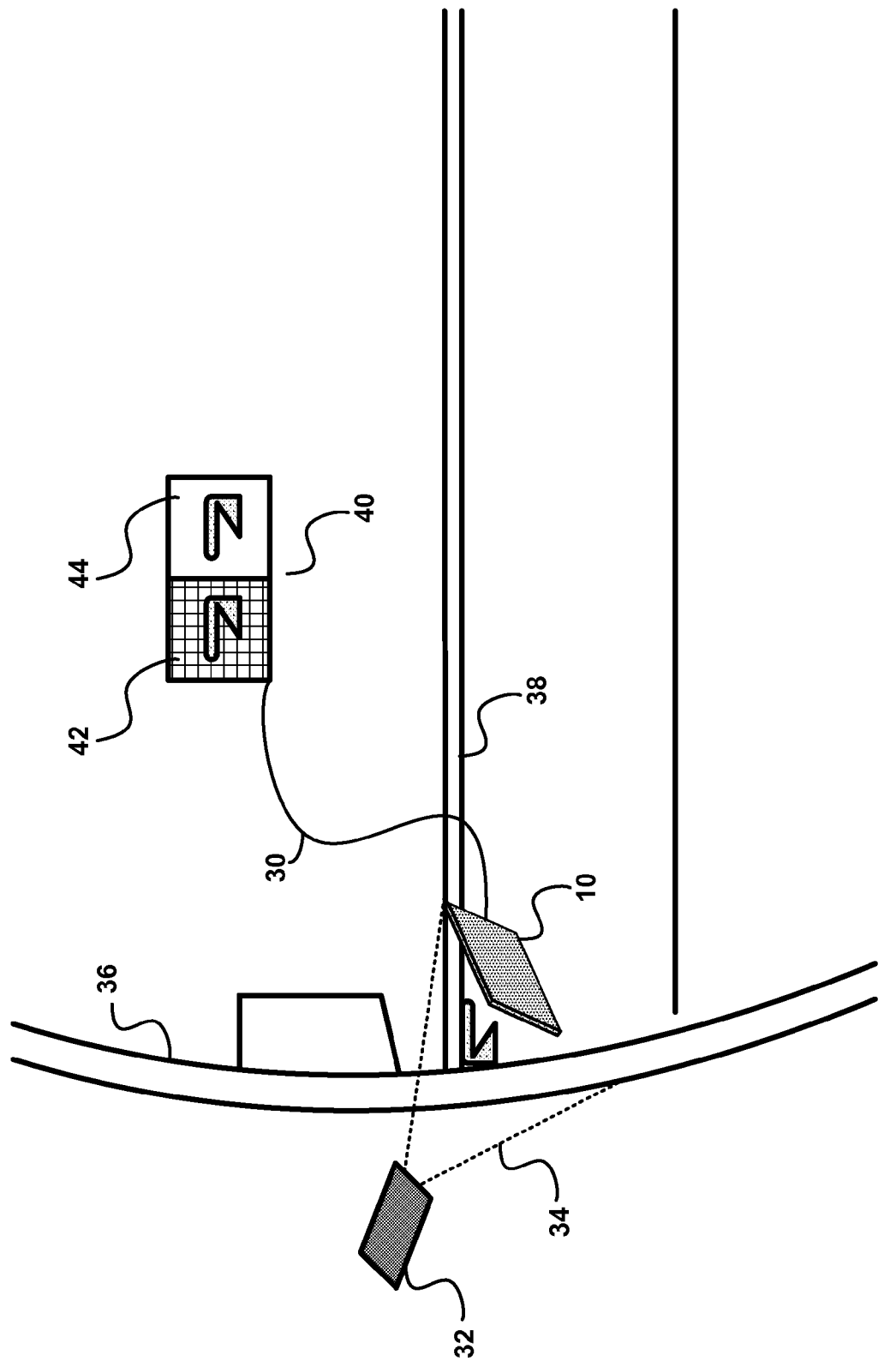
FIG. 4 shows an application of the inspection system of FIGS. 1, 2, and 3 to the inspection of aircraft structures.

FIG. 4 illustrates how an aircraft part may be inspected using the inspection system of FIGS. 1, 2, and 3. The inspection may be made in the course of manufacturing, certification, or maintenance procedures. An x-ray source 32 sends an x-ray beam 34 toward and through the joint between the fuselage 36 and floor 38 of an aircraft. The beam 34 passes through one side of the fuselage 36 and illuminates an x-ray detector 10 located on the other side of the fuselage 36. The output of the detector 10 is transmitted to a computer 40 by means of cable 30 or wireless connection, where the x-ray image 42 and the visual image 44 are displayed side by side on the display of the computer 40.

FIG. 5 shows how an inspection of a limited access area is accomplished by an inspection system like the one shown in FIGS. 1, 2, and 3. The limited access area can be any area where it is difficult to gain access for x-ray or visual inspection procedures, such as the hat stiffeners used in aircraft or the leading or trailing edge sections of an aircraft wing. The low profile detector 10 may be inserted into a narrow space 50 formed between a composite structure 46 and another structure 48 to inspect the inside surfaces of the space 50. An x-ray beam 34 is directed through structures 46 and 48. The x-ray and visual images produced by the detector 10 are again conveyed to a computer 40 and displayed as x-ray image 42 and visual image 44 as before.

The inspection system described above provides an apparatus and method of providing a real time visual image while an x-ray image is being taken, allowing superimposition or side by side comparison of the images for improved analysis and interpretation. It provides for very low profile, high resolution optical correlation of remote access x-ray inspection. This technique can be applied to any size or shape x-ray recording medium (digital or film), as long as it can lie relatively flat and provide an optical reflection that can be recorded and digitally manipulated. All of this is accomplished with a very low profile device, so very narrow spaces can be inspected.

The apparatus described above is a low profile vision system for remote x-ray inspection that allows the inspector to know exactly where the x-ray images were taken. It provides an alternative radiographic remote inspection tool to replace and/or complement the current borescope with encoder technology for locating areas that need to be x-rayed. Although the apparatus discussed above has been described as applicable to the aerospace industry, it also is useful in fields other than aerospace, including pipe welding and inspection, security, corrosion inspection, automobiles, electronics, petrochemical applications, medical applications, and others. Essentially the inspection system is applicable to any situation where x-rays need to be taken and there is a need for a visual analog of an x-ray image. For example, the inspection system can be used in dental and medical applications and oil drilling systems. It can also be used to inspect pipes, tubing, and conduits. Other applications will occur to persons skilled in the art.

The Title, Technical Field, Background, Summary, Brief Description of the Drawings, Detailed Description, and Abstract are meant to illustrate the preferred embodiments of the invention and are not in any way intended to limit the scope of the invention. The scope of the invention is solely defined and limited by the claims set forth below.

The invention claimed is:

1. An inspection system for producing an x-ray image and a corresponding visual image of an inspected part, comprising:
    an x-ray detector having a generally planar x-ray sensing surface adapted to produce an x-ray image of an inspected part;
    an x-ray transmissive and optically reflective coating covering the x-ray sensing surface; and
    at least one optical wide angle camera mounted next to the x-ray sensing surface such that the optically reflective coating is in the field of view of the optical camera, said optical camera adapted to produce a visual image of the inspected part corresponding to the x-ray image of the inspected part produced by the x-ray detector, wherein the visual image is produced from an optical image of the inspected part reflected from the optically reflective coating.

2. The inspection system of claim 1, in which the x-ray detector comprises:
    a substantially flat case;
    a scintillator array housed in the case and adapted to convert x-rays falling on the x-ray sensing surface of the detector into light energy; and
    a detector array housed in the case adapted to convert light energy from the scintillator array into electrical energy corresponding to an x-ray image detected by the x-ray detector.

3. The inspection system of claim 1, in which the at least one wide angle camera comprises a fish eye lens.

4. The inspection system of claim 1, in which the inspected part is an aircraft part.

5. The inspection system of claim 1, further comprising:
    an image storage and processing device connected to the x-ray detector and the at least one wide angle camera, the image storage and processing device adapted to store and display images produced by the x-ray detector and at least one wide angle camera.

6. The inspection system of claim 1, further comprising:
    a light emitting diode adapted to illuminate the coating.

7. A method of inspecting a part, comprising the steps of:
    passing a beam of x-rays through the part; and
    using the inspection system of claim 1 to produce an x-ray image of the part and a visual image of the part correlated to the x-ray image.

8. A method of inspecting an object, comprising the steps of:
    producing an x-ray image of the object on a planar x-ray sensing surface; and
    producing a visual image of the object that corresponds to the x-ray image, wherein the visual image is produced from an optical image of the object reflected from an x-ray transmissive and optically reflective coating covering the x-ray sensing surface.

9. The method of claim 8, wherein the object is an aircraft component.

10. The method of claim 9 wherein the method is used during a procedure selected from the group consisting of a manufacturing procedure, a certification procedure, and a maintenance procedure.

11. The inspection system of claim 1, wherein the optical axis of the camera is substantially parallel to the x-ray sensing surface.

* * * * *